United States Patent [19]

Ovaert et al.

[11] Patent Number: 5,648,087
[45] Date of Patent: Jul. 15, 1997

[54] ANAESTHETIC PHARMACEUTICAL COMPOSITION COMPRISING A GENERAL ANAESTHETIC AND SELEGILINE

[75] Inventors: Patricia Ovaert, Bordeaux; Eliane Boivin, Pompignac, both of France

[73] Assignee: Sanofi Sante Nutrition Animale, Libourne, France

[21] Appl. No.: 205,489

[22] Filed: Mar. 4, 1994

[30] Foreign Application Priority Data

Mar. 9, 1993 [FR] France ................... 93 02713
Dec. 22, 1993 [FR] France ................... 93 15496

[51] Int. Cl.$^6$ ................................ A61F 2/00
[52] U.S. Cl. ............ 424/423; 514/650; 514/657; 514/665; 514/666; 514/816; 514/817; 514/818; 564/428
[58] Field of Search ............. 424/423; 514/650, 514/657, 665, 666, 816, 817, 818; 564/428

[56] References Cited

U.S. PATENT DOCUMENTS

| | | | |
|---|---|---|---|
| 3,879,535 | 4/1975 | Stoliker | 424/273 |
| 3,896,221 | 7/1975 | Christie et al. | 424/246 |
| 4,017,619 | 4/1977 | Burnap | 424/244 |
| 4,346,110 | 8/1982 | Palfreyman et al. | 424/319 |
| 5,204,116 | 4/1993 | Edgren et al. | 428/473 |
| 5,338,550 | 8/1994 | Edgren et al. | 424/473 |

OTHER PUBLICATIONS

Gandolfi et al. "Neuroscience Letters, 165 (1994) 113–116".
DeSarro et al. "Neuropharmacology", 32(1), pp. 51–58, 1993.
Youdim et al. "European J. Pharmacology", 150 (1988) pp. 381–384.
Klockgether et al. "Brain Research", 461 (1988) pp. 343–348.

*Primary Examiner*—Helen Lee
*Attorney, Agent, or Firm*—Jacobson, Price, Holman & Stern, PLLC

[57] ABSTRACT

The present invention relates to an anaesthetic veterinary pharmaceutical composition, comprising a general anaesthetic selected from phencyclidine derivatives such as ketamine or tiletamine, as well as 0.015 to 1.25 molar equivalents of selegiline, combined in a single pharmaceutical composition or presented separately.

5 Claims, No Drawings

ANAESTHETIC PHARMACEUTICAL COMPOSITION COMPRISING A GENERAL ANAESTHETIC AND SELEGILINE

The present invention relates to pharmaceutical compositions for producing general anaesthesia in mammals, and in particular in pet animals.

In veterinary medicine, for short operations lasting less than one hour, it is common to administer to the animal ketamine or tiletamine, medicines which induce anaesthesia shortly after they are injected intravenously or intramuscularly, and which lead to a rapid awakening.

These compounds are not without side-effects, and it has been proposed to combine them with benzodiazepines, with xylazine or with acepromazine, as mentioned in JAVMA 180(12), 1462–1471 (1982).

However, these combinations prolong the duration of the anaesthesia, and are also often the source of hallucinations and of a hyperexcitability to any external stimulus during the induction phase and that of awakening.

The administration of the compositions according to the invention induces few if any hallucinations and uncoordinated movements during the induction and awakening phases; in addition, the muscular rigidity observed during anaesthesia induced by ketamine or by other phencyclidine derivatives, which is the source of convulsions, spasms and epileptiform seizures, decreases substantially for an equivalent degree of analgesia; lastly, no aggravation of the known cardiovascular effects of ketamine, in particular the hypertensive and tachycardiac effect, is observed.

The compositions according to the invention comprise a phencyclidine type general anaesthetic such as ketamine or tiletamine and their pharmaceutically acceptable salts, as well as selegiline or one of its pharmaceutically acceptable salts, combined in a single pharmaceutical composition for simultaneous administration, or presented separately for administration in close succession. In the latter case, selegiline has the role of pre-anaesthetic or restraining agent.

Tiletamine is 2-(ethylamino)-2-(2-thienyl) cyclohexanone. Ketamine is (±)-2-(2-chlorophenyl)-2-methyl-aminocyclohexanone. Selegiline (−)-N, α-dimethyl-N-(2-propynyl) phenethylamine.

The compositions can take the form of powders, lyophilized or otherwise, to be diluted at the time of use in an aqueous or oily vehicle for injection, or the form of injectable aqueous or oily suspensions or solutions in which the active ingredient may be combined with traditional adjuvants.

The single dose of composition according to the invention will contain the usual anaesthetic dose of the phencyclidine compound combined with 0.015 to 1.25 molar equivalents of selegiline, preferably 0,050 to 1.0 and advantageously from 0.25 to 1.0.

In dogs and cats in particular, there may be administered intravenously from 5 to 8 mg/kg of ketamine with 0.1 mg/kg to 5 mg/kg, in particular 0.25 mg/kg to 4 mg/kg and advantageously from 1 to 4 mg/kg of selegiline HCl in aqueous solution to obtain an anaesthesia lasting approximately half an hour; the injections will be, in general, from 0.05 to 0.5 ml/kg, and in particular from 0,125 to 0.5 ml/kg, of body weight.

It is known that the selegiline molecule contains an asymmetric carbon and that only this laevorotatory isomer is a monoamine oxidase type B inihibitor; consequently, the compositions according to the invention can also contain the d-isomer, or the racemic mixture of selegiline (also known as deprenyl) in the proportions required for the l isomer (assuming that the d isomer has little or no activity as well in the context of the present invention).

When the anaesthetic and selegiline are packaged separately, the two solutions may be mixed when required at the time of injection, or the selegiline may be administered from 5 to 20 minutes beforehand, in particular subcutaneously.

STUDY 1

Separate Solutions of Selegiline and of Ketamine

In what follows, clinical observations made during the general anaesthesia of beagle dogs, which were injected intravenously with approximately 2 to 3 ml of aqueous solution of ketamine hydrochloride and of selegiline hydrochloride in the proportions stated in Table I below, are described. Each solution was administered twice to 2 dogs with an interval of 4 days; ketamine alone had previously been administered to the same animals 5 days beforehand.

In Table I the data in the columns are as follows:

(A) : the time of induction of anaesthesia (min)
(B) : the duration of anaesthesia (min)
(C) : the time elapsing between injection and the appearance of spontaneous locomotion (min)
(D) : the time elapsing between injection and the observation of normal behaviour (min)
(E) : the degree of analgesia on pinching an ear lobe with a surgical clamp (score from 0 to 3, a score of 3 corresponding to a good degree of analgesia)
(F) : the degree of muscular relaxation on mobilisation of the animal's limbs in decubitus (score from 0 to 3, a score of 3 denoting great relaxation).
(G) : the extent of spasm type spontaneous movements (score 1), epileptiform seizure (score 2) or convulsion (score 3)

For the last 3 observations, the score indicated is the sum of the nine values recorded every 5 minutes over 40 minutes (mean value for 2 dogs).

The results show that the anaesthetic composition according to the invention, used in separate solutions, permits a short-term anaesthesia while avoiding the convulsive episodes and also poor muscle relaxation observed with ketamine alone.

TABLE I

| ketamine HCl mg/kg | selegiline HCl mg/kg | A | B | C | D | E | F | G |
|---|---|---|---|---|---|---|---|---|
| 8 | 0 | 0.42 | 16.2 | 20.3 | 40.3 | 14.7 | 2.5 | 8.2 |
| 8 | 0.125 | 0.42 | 15.5 | 18 | 32 | 11.5 | 2.5 | 2 |
| 8 | 0.500 | 0.38 | 17.5 | 20 | 35.5 | 15 | 8.0 | 3.5 |
| 8 | 1.0 | 0.35 | 15 | 19.5 | 31.5 | 13.5 | 6.0 | 0.5 |

STUDY 2

Single Solution of Ketamine/Selegiline

The composition used comprises:

| | |
|---|---|
| Ketamine HCl | 50.0 mg |
| Selegiline HCl | 10.0 mg |
| Excipient (water) q.s. | 1.0 ml |

This study is carried out on 6 beagle dogs (3 males and 3 females).

Injection is IV and of 1.6 ml/kg.

The protocol and the evaluation criteria are identical to those in Study 1. The results are collected in Table II below. The values indicated are means on 6 beagles.

TABLE II

| Parameters | A | B | C | D | E | F | G |
|---|---|---|---|---|---|---|---|
| Mean value 6 beagles | 0.45 ± 0.06 | 19.1 ± 4.6 | 26.6 ± 5.06 | 39.6 ± 7.16 | — | 6.1 | 0.68 |

This study confirms the results obtained in Study 1, but with a single solution of the composition according to the invention.

STUDY 3

Solution of Selegiline Alone Administered Subcutaneously

The concentration of the solutions varies from 1 mg/kg to 3 mg/kg. Injection of selegiline HCl was performed subcutaneously, 20 minutes before the IV injection of ketamine or of tiletamine. Each dose is tested on 4 cats (2 males and 2 females—European breed).

The electromyogram and the electroencephalogram permit the evaluation, respectively, of the parameters of muscle relaxation and of recurrent hallucinotic images which are characterized by salvos of 80 to 150 µV and 18 to 20 Hz spikes on the EEG (electroencephalogram) recording.

The results are collected in Table III below.

TABLE III

| | Behaviour before IV | Muscle relaxation | Baseline KEG activity | Response to visual, auditory, tactile stimulation | | Awakening |
|---|---|---|---|---|---|---|
| Ketamine alone 8 mg/kg | Animals very agitated | Hypertonia | 30–50 µV 10–15 Hz large amplitude considerable activity | Countless clonic muscle spasms => agitation | | Animals anxious, very agitated |
| Ketamine 8 mg/kg + 0.5 mg/kg selegiline | Animals agitated | Very moderate muscle relaxation | 5–15 µV 25–30 Hz => animals stressed | VS AS TS | persistent salvos of spikes ditto ditto | Animals anxious |
| Ketamine 8 mg/kg + 1.0 mg/kg selegiline | Animals fairly calm | Correct muscle relaxation | 5–15 µV 20–25 Hz ditto above | VS AS TS | persistent salvos of spikes ditto salvos of spikes, non-persistent | Animals fairly calm |
| Ketamine 8 mg/kg + 3.0 mg/kg selegiline | Animals very calm | Satisfactory muscle relaxation | 5–10 µV 10–20 Hz State of rest | VS AS TS | 0 0 0 | Animals very calm |
| Tiletamine (Zoletil ®: 3.75 mg/kg) | Animals very agitated | Perfect muscle relaxation | 5–15 µV 25–30 Hz Animals slightly stressed | VS) AS) TS) | persistent salvos of spikes | Animals crying, very agitated |
| Tiletamine 3.75 mg/kg (Zoletil ®: - + 3.0 mg/kg selegiline | Animals very calm | Perfect muscle relaxation | 5–10 µV 10–20 Hz State of rest | VS AS TS | 0 0 0 | Animals very calm |

VS: Visual stimulation; AS: Auditory stimulation; TS: Tactile stimulation

Study 3 demonstrated that the use of selegiline prevents recurrent hallucinotic images after ketamine or tiletamine anaesthesia, and facilitates the handling of the animals before injection of these compounds.

We claim:

1. A method for the prophylactic treatment of the side-effects due to the administration of a phencyclidine general anesthetic, comprising the intravenous administration to a mammal other than man of 0,015 to 1.25 molar equivalents of an active compound selected from selegiline and one of its pharmaceutically acceptable salts.

2. The method as claimed in claim 1, wherein the anesthetic agent is selected from ketamine, tiletamine and one of their pharmaceutically acceptable salts.

3. The method as claimed in claim 1, for the prophylactic treatment of muscular hypertonia, epilepti-form seizures and recurrent hallucinotic images.

4. The method as claimed in claim 1, wherein the anesthetic agent and said active compound are administered simultaneously.

5. The method as claimed in claim 1, wherein said anesthetic agent and said active compound are administered separately.

* * * * *